United States Patent [19]

Yi

[11] Patent Number: 5,409,499

[45] Date of Patent: Apr. 25, 1995

[54] BIOCOMPATIBLE SUTURE KNOT CLIP

[75] Inventor: Sung S. Yi, Princeton, N.J.

[73] Assignee: Ethicon, Inc., Somerville, N.J.

[21] Appl. No.: 80,039

[22] Filed: Jun. 18, 1993

[51] Int. Cl.⁶ ............................................. A61B 17/00
[52] U.S. Cl. ..................... 606/151; 606/157; 227/902; 24/470; 24/477; 24/545; 24/547
[58] Field of Search ............... 606/151, 157, 158, 221; 227/902; 128/831, 843; 24/543, 542, 530, 517, 518, 528, 545, 555, 464, 406, 469, 470, 477

[56] References Cited

U.S. PATENT DOCUMENTS

| 4,545,377 | 10/1985 | Cerwin et al. | 606/158 |
| 4,686,983 | 8/1987 | Leisman et al. | 606/158 |
| 5,078,731 | 1/1992 | Hayhurst . | |
| 5,160,339 | 11/1992 | Chen et al. | 606/158 |
| 5,234,449 | 8/1993 | Bruker | 606/158 |
| 5,282,811 | 2/1994 | Booker et al. | 606/151 |

FOREIGN PATENT DOCUMENTS 2932652 2/1981 Germany ............... 606/151

Primary Examiner—Stephen G. Pellegrino
Assistant Examiner—Jeffrey A. Schmidt
Attorney, Agent, or Firm—Hal Woodrow

[57] ABSTRACT

A sterile one-piece suture clip having a first clamping member having a distal end, a first proximal end and a first clamping surface, a second clamping member having a second proximal end, a second clamping surface, and a locking surface and being pivotally connected at said second proximal end by a hinge to said first proximal end of the first clamping member, a plurality of leg members each having an inner surface, a side surface and an end, said legs being disposed in sets comprising U-shaped members in combination with the first clamping surface, the inner surface of each leg in the set facing the opposite leg thereof, said inner surface being beveled from the end of the leg toward the first clamping surface to form ears, said U-shaped members being attached to the first clamping member, said side surface of said legs being beveled from the end of the leg toward the first clamping member thereby forming a channel said first clamping member being adapted to be placed on a suture to be clipped, said channel being adapted to orient a suture transversely across said first clamping surface and said second clamping member being sized and configured to pivot about said hinge, extend between and fit within each of said U-shaped members, be held in place by said ears engaging said locking surface thereby engaging a suture between said first and second clamping surfaces.

4 Claims, 3 Drawing Sheets 5,409,499

BIOCOMPATIBLE SUTURE KNOT CLIP

FIELD OF INVENTION

The present invention relates to a surgical clip. More particularly, it relates to a clip suitably adapted to replace a suture knot during endoscopic surgery.

BACKGROUND OF THE INVENTION

One of the truly great advances in recent years to reduce the invasiveness of surgical procedures is endoscopic surgery. Endoscopic surgery involves the use of an endoscope which is an instrument permitting the visual inspection and magnification of any cavity of the body. The endoscope is inserted through a cannula after puncture through the wall of the body cavity with a trocar, which is a sharp-pointed instrument. The surgeon can then perform diagnostic and therapeutic procedures at the surgical site with the aid of specialized instrumentation designed to fit through additional cannulas providing small diameter openings into the desired body cavity as may be required.

An age-old procedure which surgeons are required to perform to repair or reconstruct traumatized bodily tissue is suturing. Fortunately, medical instruments have been recently designed to allow a surgeon to manipulate a suture, or suture and needle combination, through the small diameter opening of a cannula. However, the ability to accurately place and securely tie a suture knot had become troublesome and problematical.

Therefore, in response to this problem, surgeons have sought alternatives to conventional knot-tying techniques which would be suitable during endoscopic surgery. Among these alternatives include the use of hemostatic clips, which are designed to ligate blood vessels and other tubular members, to replace suture knots. Such hemostatic clips are described, for example, in U.S. Pat Nos. 4,418,694 and 4,476,865. These clips can be readily applied with a clip applier which is designed to function through the small opening of a cannula. Unfortunately, the force required to displace these clips from a suture is too low to provide a secure knot. As a result, hemostatic clips of the type shown in the art are unsuitable for use as endoscopic knot clips.

In view of the deficiencies of the prior art for creating a useful alternative to tying a suture knot, what is desired within the medical community is a device suitable for application using endoscopic techniques which can successfully replace the suture knot. More specifically, what is needed is a clip particularly adapted for replacing a suture knot during endoscopic surgery, and which exhibits adequate clamping force to function effectively.

SUMMARY OF INVENTION

The present invention provides a sterile one-piece suture clip comprising a first clamping member having a distal end, a first proximal end and a first clamping surface; a second clamping member having a second proximal end, a second clamping surface, and a locking surface and being pivotally connected at said second proximal end by a hinge to said first proximal end of the first clamping member; a plurality of leg members each having an inner surface, a side surface and an end, said legs being disposed in sets comprising U-shaped members in combination with the first clamping surface, the inner surface of each leg in the set facing the inner surface of the opposite leg thereof, said inner surface being beveled from the end of the leg toward the first clamping surface to form ears, said U-shaped members being attached to the first clamping member, said side surface of said legs being beveled from the end of the leg toward the first clamping member thereby forming a channel; said first clamping member being adapted to be placed on a suture to be clipped, said channel being adapted to orient a suture transversely across said first clamping surface and said second clamping member being sized and configured to pivot about said hinge, extend between and fit within each of said U-shaped members, be held in place by said ears engaging said locking surface thereby engaging a suture between said first and second clamping surfaces.

BRIEF DESCRIPTION OF THE FIGURES

The present invention will be described in great detail in conjunction with the accompanying figures.

DETAILED DESCRIPTION OF THE INVENTION

Figure 1:
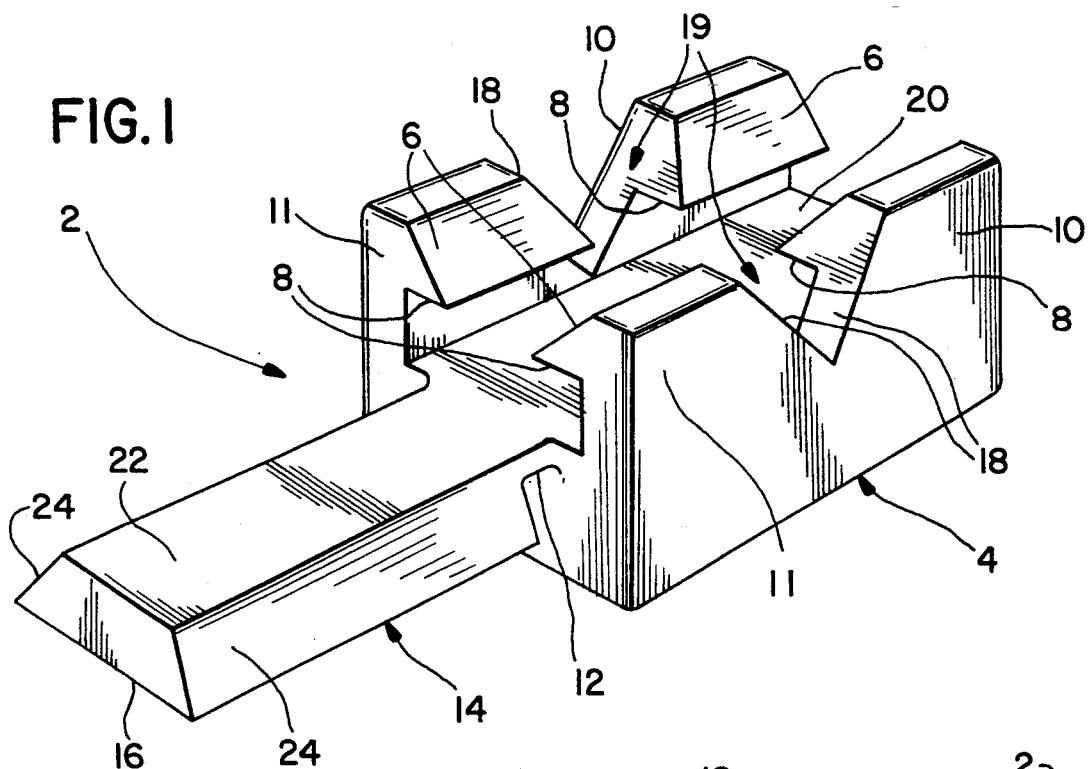
FIG. 1 is a greatly enlarged perspective view of a clip in accordance with the present invention.
Figure 2:
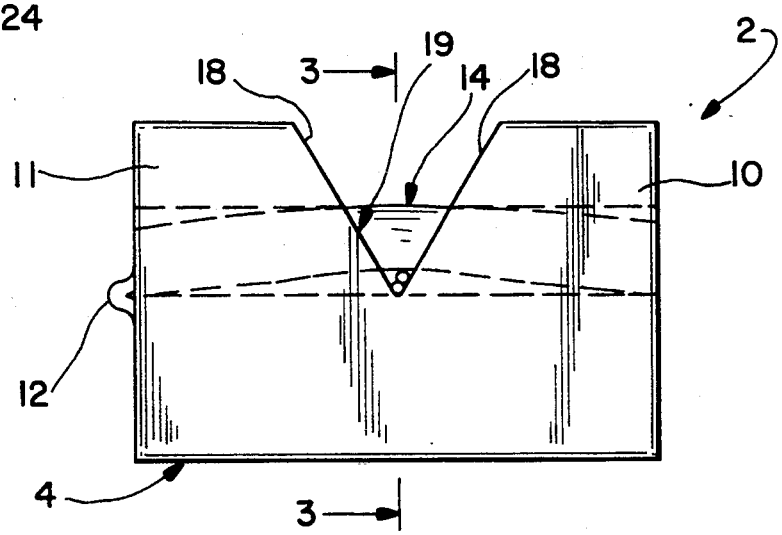
FIG. 2 illustrates the clip of FIG. 1 clamped about a suture.

Referring to FIG. 1 there is shown a surgical suture clip of the present invention. The clip 2 has a first and second clamping members 4 and 14 respectively. The clamping members are connected at their proximal ends by a hinge section 12. The hinge section according to the present invention is resilient and aids in the handling and placement of the clip. The first clamping member 4 is horizontal and has a first clamping surface 20 and several sets of leg members, preferably two sets of leg members 10 and 11 as shown in FIG. 1. Each set of legs forming a U-shape when attached to the first clamping member. Preferably two sets of leg members will be disposed at opposite ends of the first clamping surface 20.

Each leg of the U-shaped leg members has a beveled inner surface 6 extending from the free end of the leg toward the first clamping surface 20 and terminating at an ear 8. Additionally, each leg of the U-shaped leg members also has a side surface 18 extending from the free end of the leg toward the first clamping member 4. The side surfaces 18 of adjacent side by side set of leg members 10 and 11 form a channel or groove 19 between the sets of leg members 10 and 11. The second clamping surface 14 comprises a second clamping surface of 22 and a locking surface 16. Additionally the second clamping member 14 also may have a beveled outer surface 24 extending from the locking surface to the second clamping surface.

Figure 4:
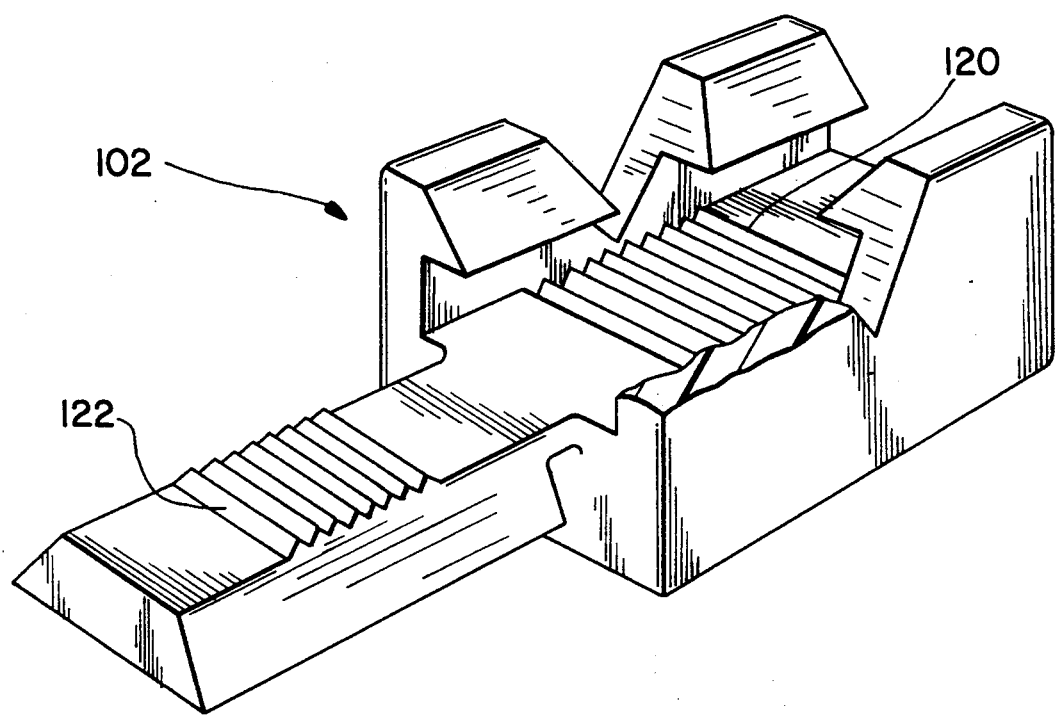
FIG. 4 illustrates a suture clip in accordance with one embodiment of the invention wherein the clamping surfaces have been scored.

In another embodiment of the invention, the clamping surfaces may be textured by grooves, dimples, cross hatching, scoring or the like. In a preferred embodiment, as illustrated in FIG. 4, the clamping surfaces 120 and 122 are scored or grooved to grip the suture more securely when the clip 102 is closed.

Figure 3:
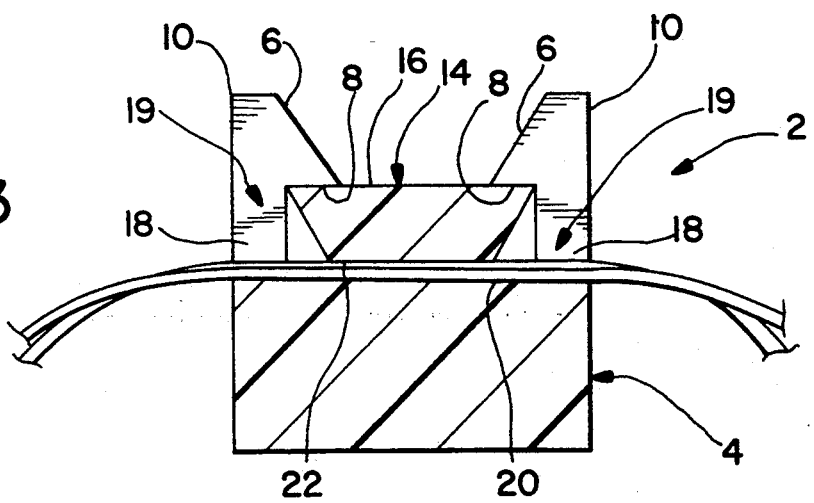
FIG. 3 is a cross-sectional view taken along line 3—3 of FIG. 2.

The suture clip 2 is employed by placing a suture or sutures of an appropriate diameter transversely across the first clamping surface 20 and between the two sets of legs 10 and 11 in channel 19. The second clamping member 14 is then pivoted about the hinge 12. As the second clamping member 14 pivots it contacts the leg members 10 and 11 on beveled inner surface 6 and deflects the legs outward until the flat locking surface of the second clamping member passes by the ears 8 and the legs snap back to lock the second clamping member in place. See FIG. 3 for a cross-sectional view of a closed suture clip and sutures. The suture is securely held in place by the force exerted by the first and second clamping surfaces respectively 20 and 22. The clamping surface should be formed to be complementary and may be curved but are preferably flat.

Figure 5:
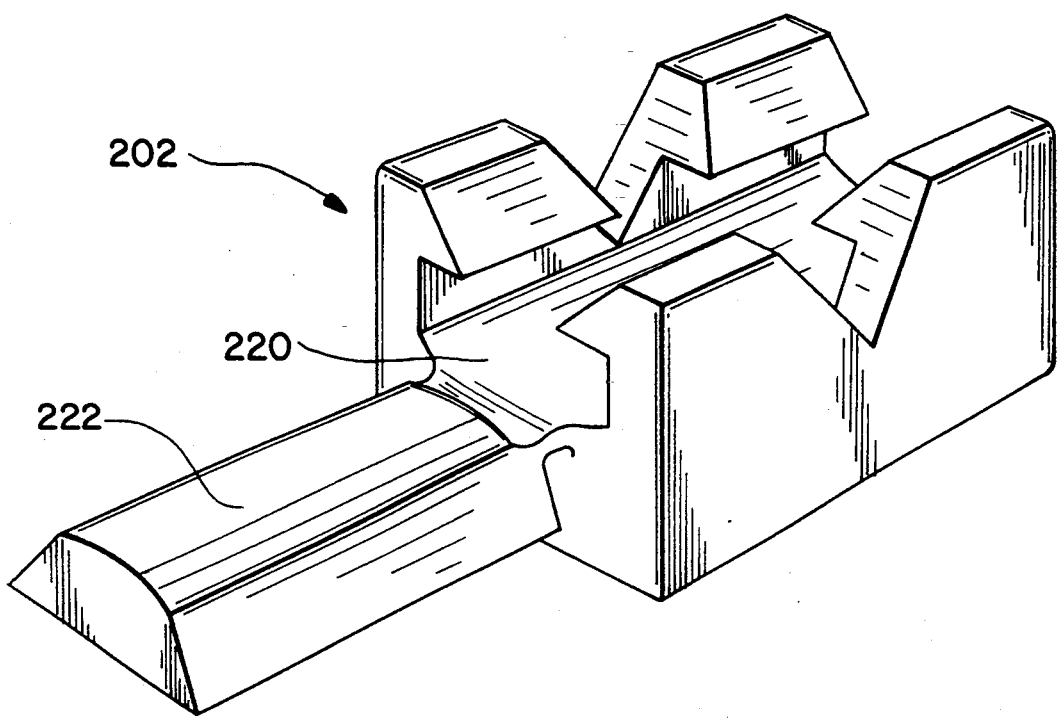
FIG. 5 illustrates a suture clip in accordance with one embodiment of the invention wherein the clamping surfaces have complementary curved surfaces.
Figure 6:
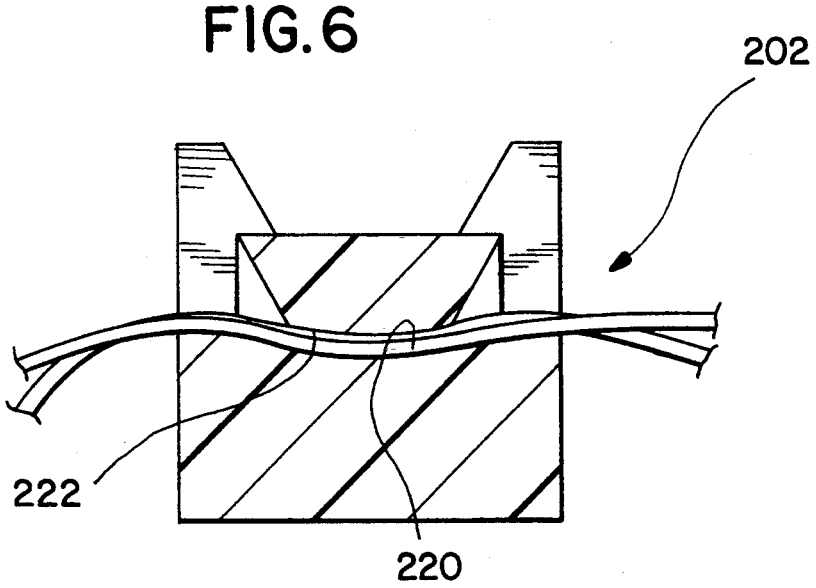
FIG. 6 is a transverse cross-sectional view of the clamp of FIG. 5.

In an alternative embodiment of the present invention as shown in FIG. 5 and FIG. 6 the second clamping surface 222 of said second clamping member has a convex radius of curvature extending transversely across substantially the entire width of said second clamping member, and the first clamping surface 220 of said first clamping member has a concave radius of curvature extending transversely across substantially the entire width of said first clamping member. The radius of curvature of the second clamping surface 222 of said second clamping member is being smaller than the radius of curvature of the first clamping surface 220 of said first and second clamping members being complementary and when the clip 202 is in a clamped position. The clamping surfaces of said first and second clamping members are in substantially complete contacting relationship so as to minimize the gap which is created between said surfaces when the clip is closed.

The clips of the present invention may be constructed in various sizes according to their intended function. Suture clips are usually less than 10 millimeters in length and 10 millimeters in width. The dimension of the clip may be reduced by about 50% for certain applications in microsurgery. Larger clips for special suture applications may be about double the size of a typical suture clip. The various sizes of the clip are preferably matched with individual appliers having jaws tailored to the size of the clip for best performance.

The clips of the invention can be made of any biocompatible material using conventional fabrication methods. The clips can be composed of various biocompatible metals, e.g. titanium and tantalum, and polymeric materials. Preferred bioabsorbable polymeric materials include homopolymers and copolymer of epsilon-caprolactone, glycolide, lactide and para-dioxanone. Preferred non-absorbable polymers include nylons, polyesters and polypropylene. All these materials have been demonstrated to be biologically acceptable when used as sutures or other implantable medical devices.

The preferred means for fabricating clips from polymeric materials is to inject a suitable polymer melt into an appropriately designed mold at process conditions conventionally employed for such polymer systems. After the polymer melt cools, the molded polymer shaped in the mold to meet the design criteria of the clip can be readily released from the mold.

The clips are sterilized by any of the well known sterilization techniques and the technique selected will depend to a great extent on the material used to make the clip. Suitable sterilization techniques include heat or steam sterilization, radiation sterilization (such as cobalt irradiation, electron beam and the like), ethylene oxide, and other sterilization techniques well known in the art.

Having now described the present invention and certain specific embodiments thereof, it will be readily apparent to those skilled in the art that many variations and modifications may be made to the present invention without departing from the spirit and scope thereof.

What is claimed is:

1. A sterile one-piece suture clip comprising:
   a first clamping member having a distal end, a first proximal end and a first clamping surface;
   a second clamping member having a second proximal end, a second clamping surface, and a locking surface and being pivotally connected at said second proximal end by a hinge to said first proximal end of the first clamping member;
   at least four leg members each having an inner surface, a side surface and an end, said legs being disposed in sets comprising U-shaped members in combination with the first clamping surface, the inner surface of each leg in the set facing the inner surface of the opposite leg thereof, said inner surface being beveled from the end of the leg toward the first clamping surface to form ears, leg members being attached to the first clamping member, said side surface of said legs being beveled from the end of the leg toward the first clamping member thereby forming a channel;
   said first clamping member for placement on a suture to be clipped, said channel for orienting a suture transversely across said first clamping surface and said second clamping member being sized and configured to pivot about said hinge, extend between and fit within each of said U-shaped members, and be held in place by said ears engaging said locking surface thereby engaging a suture between said first and second clamping surfaces.

2. The clip of claim 1 wherein the second clamping surface of said second clamping member has a convex radius of curvature extending transversely across substantially the entire width of said second clamping member, the first clamping surface of said first clamping member has a concave radius of curvature extending transversely across substantially the entire width of said first clamping member, the radius of curvature of the second clamping surface of said second clamping member being smaller than the radius of curvature of the first clamping surface of said first and second clamping members being complementary and when the clip is in a clamped position, the clamping surfaces of said first and second clamping members are in substantially complete contacting relationship so as to minimize the gap which is created between said surfaces.

3. The clip of claim 2 wherein said radii of curvature of the clamping surfaces of said first and second clamping members are uniform.

4. The clip of claim 1 wherein the clamping surfaces are textured.

* * * * *